(12) United States Patent
Beller

(10) Patent No.: US 7,497,390 B2
(45) Date of Patent: Mar. 3, 2009

(54) DEVICE FOR THE SPRAYING OF FLUIDS

(75) Inventor: Klaus-Dieter Beller, Kenzingen (DE)

(73) Assignee: Braunform GmbH, Bahlingen (DE)

( * ) Notice: Subject to any disclaimer, the term of this patent is extended or adjusted under 35 U.S.C. 154(b) by 616 days.

(21) Appl. No.: 10/475,671

(22) PCT Filed: Apr. 24, 2002

(86) PCT No.: PCT/DE02/01492

§ 371 (c)(1),
(2), (4) Date: Oct. 23, 2003

(87) PCT Pub. No.: WO02/087777

PCT Pub. Date: Nov. 7, 2002

(65) Prior Publication Data

US 2004/0135002 A1 Jul. 15, 2004

(30) Foreign Application Priority Data

Apr. 30, 2001 (DE) ................ 101 21 232

(51) Int. Cl.
*B05B 9/043* (2006.01)
(52) U.S. Cl. ............... 239/333; 222/83.5; 222/183; 222/321.9; 222/383.1
(58) Field of Classification Search ........... 239/289, 239/333, 338; 222/5, 83.5, 183, 321.1, 321.7, 222/321.9, 383.1
See application file for complete search history.

(56) References Cited

U.S. PATENT DOCUMENTS

| | | | | | |
|---|---|---|---|---|---|
| 2,966,283 | A | * | 12/1960 | Darvie | 222/183 |
| 4,118,830 | A | * | 10/1978 | Weiland | 452/131 |
| 4,526,302 | A | * | 7/1985 | Brunet | 222/321.7 |
| 5,335,824 | A | | 8/1994 | Weinstein | 222/82 |
| 5,595,326 | A | * | 1/1997 | Bougamont et al. | 222/321.7 |
| 5,860,543 | A | * | 1/1999 | Decelles | 215/209 |
| 6,073,805 | A | * | 6/2000 | Gueret | 222/95 |
| 6,131,567 | A | | 10/2000 | Gonda et al. | 128/200.14 |

FOREIGN PATENT DOCUMENTS

JP 55-82335 6/1980
JP 59-17358 1/1984

* cited by examiner

*Primary Examiner*—Christopher S Kim
(74) *Attorney, Agent, or Firm*—Gudrun E. Huckett

(57) ABSTRACT

A device for spraying a liquid, wherein the liquid is contained in a container that, in an initial state, is a unitary closed container comprising a head to be broken off or sawed off for providing the removal opening, has a spraying device to be arranged on the removal opening of the container. The spraying device has a basic spraying unit and a connecting adapter for the container, wherein the connecting adapter is fixedly connected to the spraying unit. The connecting adapter has an annular seal that rests sealingly on the container. The connecting adapter is essentially cylindrical and has a lower peripheral end provided with the annular seal. A sleeve having an upper open end and a lower end is provided. The lower end of the sleeve has a bottom. The sleeve receives the container. The sleeve is connected with the upper open end to the connecting adapter.

2 Claims, 3 Drawing Sheets

DEVICE FOR THE SPRAYING OF FLUIDS

BACKGROUND OF THE INVENTION

The invention relates to a device for spraying liquids wherein the liquid is contained in a container having a removal opening, comprising a spraying device to be arranged on the removal opening of the container.

A special field of application of the invention is the administration of active ingredients present in a liquid in an ampule, in particular, those to be administered by injection, for the human or animal body. However, the spraying device according to the invention is also suitable for spraying other liquids of any kind.

In the therapeutic field, pharmacological active ingredients can be administered by injections. However, in certain situations this is problematic, for example, in the case of patients having a phobia with regard to injections, which is the case particularly for children and elderly patients. Also, there are patients with inadequate vein conditions where an injection is possible only with difficulty or not at all. Also, in the case of restless patients, in particular, children and psychologically unstable persons, it is often not possible to administer an injection. Also, emergency patients can be in a state in which injections cannot be administered.

For this reason, in addition to nose sprays, which have been common for a long time (see, for example, LIST, Paul Heinz: Arzneiformenlehre, Stuttgart, WVGmbH, 1976, pp. 7ff), an alternative method for injection is proposed in U.S. Pat. No. 6,131,567 A according to which formulations are administered as aerosols in the case of active ingredients such as insulin.

In this way, an alternative is provided to the conventional administration form of active ingredients present in a liquid and designed for injections for the human or animal body. The basic idea resides in a spray as a medicament form for the absorption of active ingredients. The administration of pharmacological active ingredients is not carried out by injection but the liquid is sprayed in atomized form onto the mucous membrane of the patient, for example, in the throat or nose area. This atomized mist is distributed on the mucous membrane and is resorbed by the body. The mucous membrane has a large surface area as well as excellent blood flow and therefore provides an ideal absorption location for medicaments. With a corresponding mechanical device, a mucosal application of medicaments contained in ampules or flasks or vials by means of a corresponding spraying unit is possible. In this way, effects are enabled which significantly increase the bandwidth of use of known and future ampule goods for different medical treatments.

The advantages are the following:
cannula and syringe are no longer necessary;
increase of the application safety by avoiding infections, needle injuries in the patient and physicians as well as after bleeding at the injection location as well as no hematoma formation;
easy accessibility of the application location, even in an emergency situation;
the medicaments are not subjected to the damaging acidic medium of the stomach (gastrointestinal decomposition);
therapeutic active ingredient concentrations can be reached much quicker for different medicaments than for gastrointestinal absorption;
the first pass effect in the liver is prevented (metabolic decomposition);
resorting to oral medication can be avoided;
more uniform efficacy over time;
there is no risk of infection (AIDS, hepatitis);
conventional ampule goods are available without renewed approval for sublingual, buccal and nasal therapy;
treatment of large populations (for example, in the Third World).

Suction filters for protecting a medium or active ingredient are disclosed in DE 196 10 457 A1, and penetrable plugs (septum) in the removal opening are disclosed in WO 95/00195 A1.

It is an object of the invention to provide a system for spraying liquids that can be easily handled and that is safe.

The technical solution is characterized in that the container in its initial state is a unitary closed container, in particular, an ampule, comprising a head to be broken off or sawed off for providing the removal opening, wherein the spraying device is comprised of a basic spaying unit and a connecting adapter for the container fixedly arranged thereon, and wherein the connecting adapter has an annular seal resting sealingly on the container.

Accordingly, a safe system for spraying liquids that is easy to handle is provided. The basic idea resides in the combination of a special container of glass or plastic for the liquid to be sprayed, like an ampule, with a special spraying device. The spraying device is placed onto the container containing the liquid in order to spray by means of this spraying device the liquid contained in the container. As discussed above, the container can be an ampule like those used conventionally for injections. It is only required to break off the head of the ampule and to place the spraying device onto the thus provided removal opening. Instead of the ampule, it is also possible to provide a correspondingly configured flask containing several dosage units. In this connection, the spraying device is placed in an air-tight and liquid-tight way onto the removal opening of the container. For this purpose an annular seal is provided. In the case of ampules, this annular seal compensates decisively the break-off location that is not always exactly uniform. In the case of other containers an absolute seal tightness is provided also at any time, in particular, when the containers vary slightly with regard to their shape. By means of the spraying device a mechanical device is made available in order to spray in a simple way the liquid to be applied onto the desired mucous membrane. In this way, a standardized system is provided that is suitable for daily use and enables the user without unacceptable expenditure to administer the contents of the ampule. Accordingly, the system is suitable for many fields of injection. The mechanical device for the mucosal application of medicaments contained in ampules by means of a pump spraying unit is comprised of a pump, a spray head, an ampule connector as well as an ampule fixation unit. As already mentioned in the beginning, other types of liquids contained in the container are also suitable.

The spraying device is formed according to the invention of two basic components. The basic component is a basic spraying unit, i.e., a universal spraying device usable in connection with very different containers. The individual adaptation to the respective container is realized by means of a second component, i.e., the connecting adapter. It is individually and seal-tightly placed onto the basic spraying unit. By means of this connecting adapter a proper connection to the container in question is provided. The advantage of this system resides in its low costs because only a single basic spraying unit is required. The connecting adapters, on the other hand, are simple with regard to their manufacture. With a select assortment, it is thus possible to adapt to any container. The base spraying unit can be a commercially available unit but also a special embodiment. The base spraying unit as well as the connecting adapter can be fixedly connected to one another. In regard to greater flexibility, the two components can also be exchangeable in order to employ, as described above, a basic pump system with different metering volumes.

In order to arrange the container, in particular, the ampule, on the spraying unit, a holder for the container can be provided on the spraying unit. In this way, an ampule fixation is provided which ensures that before and during administration a fixed connection between the spraying device and the container is ensured without the spraying device becoming detached from the container.

The general advantages are as follows:
maximum actuation safety;
simple use;
metering precision;
gentle treatment of the product;
reduction of time expenditure and material costs.

There are three different kinds of the seal. In the variant with the shoulder, the annular seal rests from above on this shoulder. In the variant with the outer peripheral surface, the annular seal rests externally on the actual jacket (i.e., below the shoulder) of the container while in the last variant the annular seal is inserted into the removal opening.

As already mentioned above, the spraying device is preferably a pump spraying device. After pressing down the actuating button, vacuum is generated in the spray head upon subsequent automatic upward movement of the actuating button and the vacuum sucks in the liquid contained in the container through the ascending pipe into the spray head. During the subsequent downward pushing of the actuating button, the suction channel is closed and the liquid located in the spray head, into which is has been sucked in previously, is pushed out through the nozzle. The advantage of this system in comparison to a pump system employing overpressure in the container resides in that no airtight sealing of the spray head relative to the container is required. In this way, a simple mechanical device for technical realization of the spraying device is provided. Moreover, by means of the pump system metering is reproducible in a simple way. The metering volume can be 0.01 ml/stroke to 0.2 ml/stroke. By means of this pump spray device with the preset stroke volume it is possible to administer defined dosages of the corresponding agent as desired and needed. Also, the number of pump strokes can be adjusted, i.e., limited. Instead of conveying the liquid by means of a pump system, other conveying systems are conceivable which fulfill the corresponding purpose and supply the liquid to the spray head.

The advantage of the embodiment where a microfilter is correlated with the air inlet of the spraying device resides in germ protection.

In principle, the container can be placed upside-down with the opening facing downwardly. In this way, the ascending pipe is not needed. Another embodiment however suggests the use of the aforementioned ascending pipe. In this way, the spray device is at the top and can therefore be actuated more easily.

The embodiment comprising an ascending pipe that is exchangeable or has predetermined break-off locations for shortening it has the advantage that the ascending pipe in accordance with the desired purpose can be matched to the length of the ampule, respectively.

It also possible to use a container in the form of a storage flask closed by a septum in place of an ampule. In this case, the ascending pipe has a piercing pin with which the septum is pierced.

The embodiment according to which the spraying device, in particular, the ascending pipe has a microfilter for the liquid correlated therewith has the advantage that contaminants, which can reach the liquid during or after opening of the ampule, can be filtered out.

The embodiment according to which a holder for the container is formed by at least one stay extending in the longitudinal direction of the container on which at least one clamping arm engaging the container is arranged provides a technically simple holder. The basic idea resides in that a stay is arranged on the spraying device which extends in the longitudinal direction of the container and serves as an ampule guide. This stay provides a parallel guiding action for the ampule and prevents canting. The contact pressure can be ensured by a spring play or a guide sleeve or by hand. A flexible ampule fixation with locking action for a variable length of the guide stay enables the use of all conventional ampule sizes.

The embodiment according to which one clamping arm pair is embodied like pliers has the advantage that the container is safely held by the pliers-like engagement of the container.

The embodiment according to which the cross-section of the clamping arm pair is oval has the advantage that there is always sufficient contact pressure of the clamping arms against the ampule as a result of the non-circular cross-section.

The spray head can also be attached by means of a screw connection or a bayonet closure on the container as an alternative to the described holder. For example, it is conceivable that the conventional ampules, septum flasks or vials can be provided additionally in the area of the removal opening with an outer thread.

A further preferred embodiment of the holder proposes that the container is received in a sleeve provided at the lower end with a bottom and that the sleeve with its upper open end is pushed or screwed onto the connecting adapter. The basic idea resides in that the container, in particular, the ampule with the broken-off head end, is inserted into the sleeve and, subsequently, the connecting adapter is placed or screwed onto it from above until the annular seal contacts the shoulder of the container. In this way, a holder for the container is provided in which the container is safely arranged and protected in the spraying device. Moreover, together with the stay a compact configuration is provided by means of the connecting adapter that is placed on or screwed on.

There are different types of connections between the sleeve and the connecting adapter. In the case of a detachable locking action, a reuse of the system is possible in that, after use of the connecting adapter, it is removed from the sleeve. The detachable connection can be realized, for example, by locking elements in the form of peripheral ribs. The non-detachable connection between the sleeve and the connecting adapter is designed for disposable devices. With a corresponding configuration of the locking elements, a non-detachable design can be provided. Also, a bayonet closure can be employed for providing a detachable connection.

The embodiment according to which the connecting adapter is essentially cylindrical and provided at its lower peripheral end with the annular seal has the advantage that by means of the cylindrical configuration of the connecting adapter and the matching cylindrical configuration of the sleeve, a relatively large contact surface and thus safe fixation of the connecting adapter within the sleeve is ensured. In particular, it is possible in this way to use different containers of different height in one and the same system by means of the corresponding length adjustment of the sleeve as well as of the connecting adapter. The annular seal at the lower end of the connecting adapter is preferably a seal attached by injection-molding so that the connecting adapter and the annular seal form a unitary component. The material of the annular seal is a different material than the material of the connecting adapter.

A further preferred embodiment suggests that a spray head is arranged exchangeably on the spray device. The advantage of this exchangeable spray head resides in that all conventional or future adapters, for example, a throat adapter with or without a beak, nose adapters etc. can be used as needed.

BRIEF DESCRIPTION OF THE DRAWINGS

Three embodiments of the device according to the invention will be described in the following with the aid of the drawings. They show.

DESCRIPTION OF PREFERRED EMBODIMENTS

Figure 3:
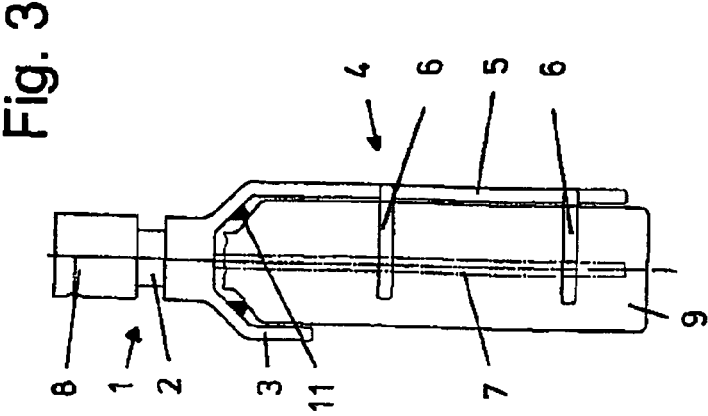
FIG. 3 a longitudinal section of the system in FIG. 2.
Figure 2:
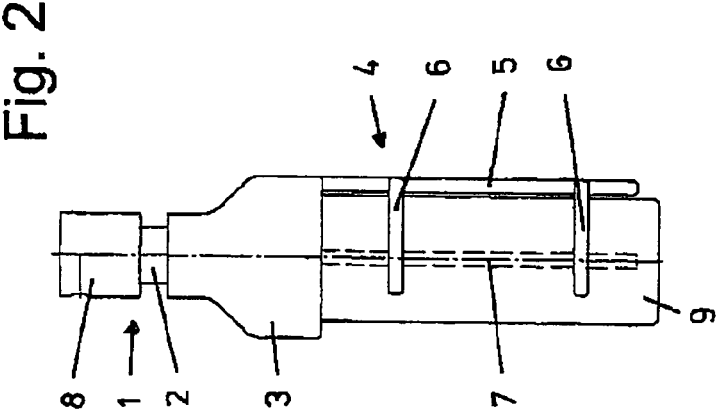
FIG. 2 the embodiment of FIG. 1 after insertion of the ampule.
Figure 1:
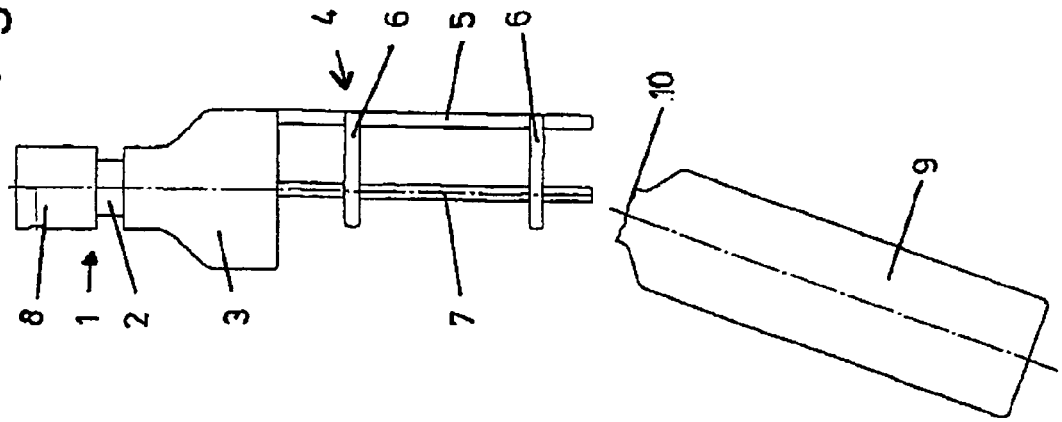
FIG. 1 a first embodiment before insertion of an ampule.
Figure 4:
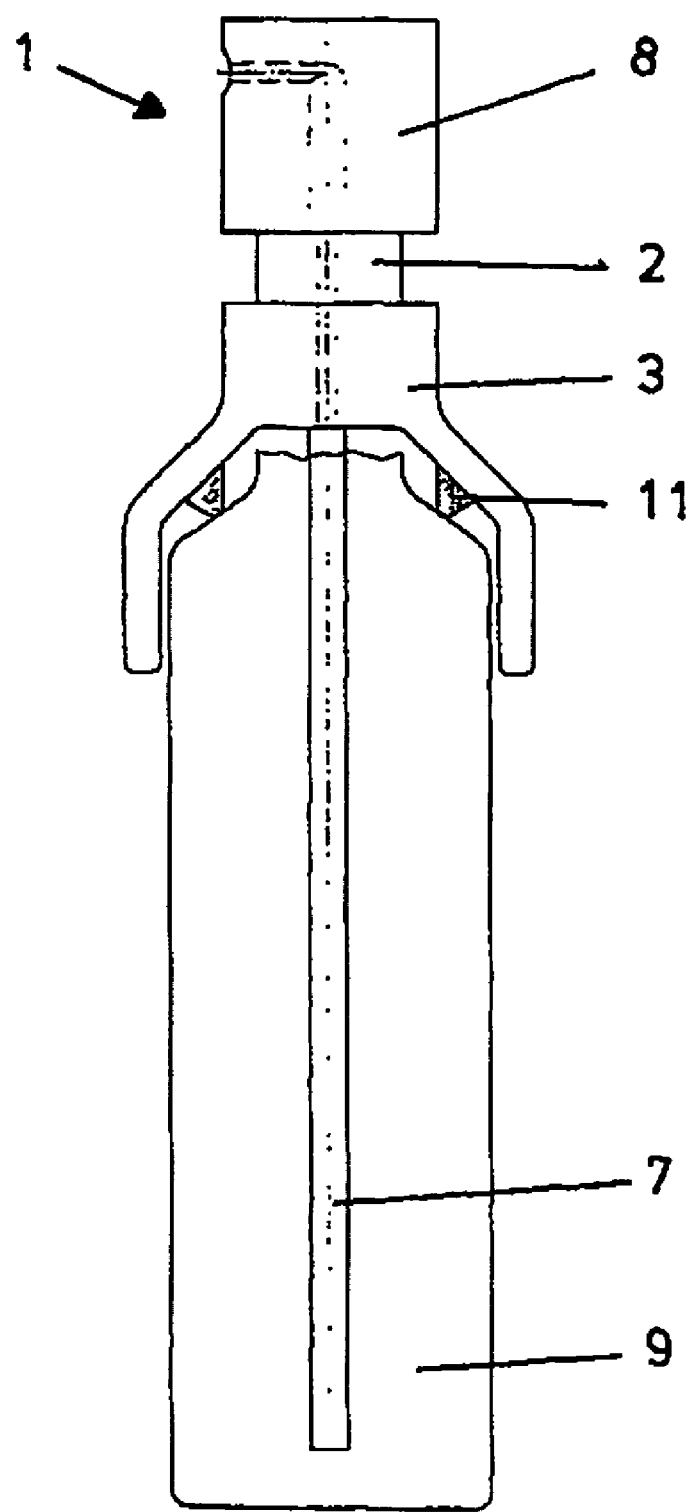
FIG. 4 a longitudinal section of a second embodiment.
Figure 5A:
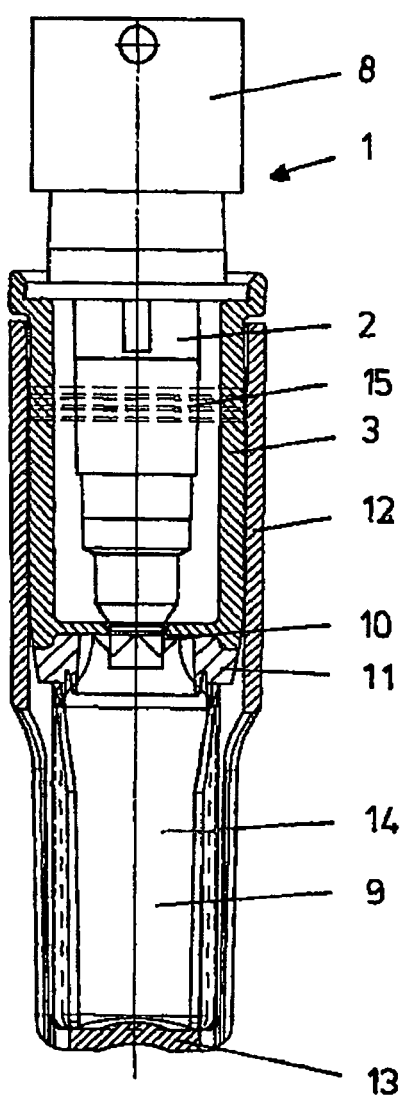
FIGS. 5a and 5b a longitudinal section of a third embodiment.
Figure 5B:
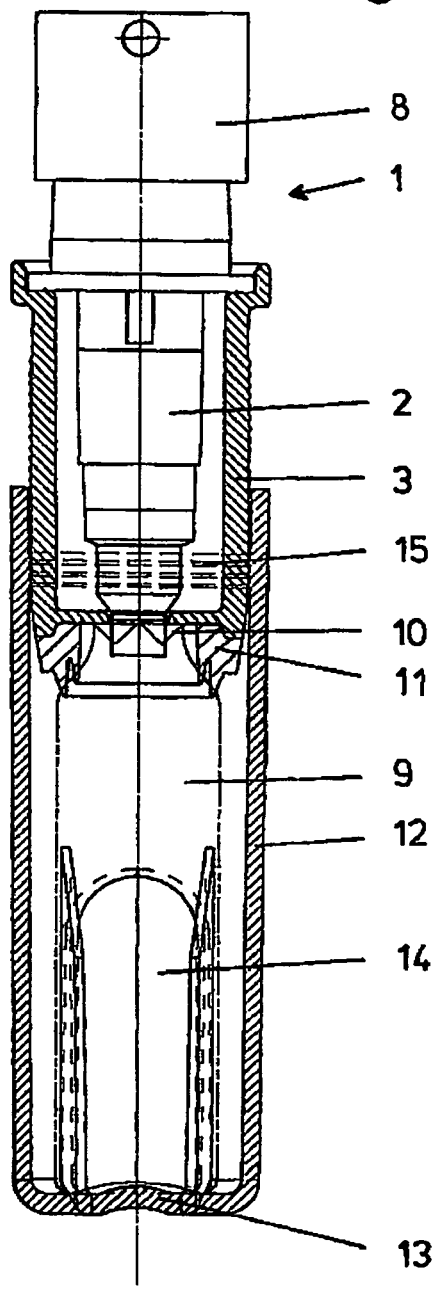

In FIGS. 1 to 3, a first embodiment, in FIG. 4 a second embodiment, and in FIGS. 5 and 5b a third embodiment of the device for administering a medicament contained in an ampule are illustrated.

The first embodiment of FIGS. 1 through 3 has a spraying device 1. It is comprised of a basic spraying unit 2 as well as a connecting adapter 3. This connecting adapter 3 is pushed onto the basic spraying unit 2 from below. Depending on the application, different shapes of connecting adapters 3 can be used.

A holder 4 is arranged on the connecting adapter 3. It is comprised of a stay 5 extending in the longitudinal direction. Two clamping arm pairs 6 are arranged thereon one above the other.

The spraying device 1, i.e., its basic spraying unit 2, has at the bottom side an ascending pipe 7 and a spray head 8 at the topside. The spray head is exchangeable and thus adaptable to any desired application.

The function is as follows:

The spraying system is to be connected to a container 9 that is in the form of an ampule and filled with a medicament. For this purpose, first the glass head of the container 9 is broken off, as indicated in FIG. 1. Subsequently, the container 9 is inserted from below along the stay 5 of the holder 4 into the connecting adapter 3 of the spraying device 1. For this purpose, the ascending pipe 7 projects into the removal opening 10 of the container 9. As indicated in FIG. 3, the upper shoulder of the container 9 contacts seal-tightly the annular seal 11 in the interior of the connecting adapter 3. The container 9 is secured in this position by the clamping arms 6. Upon actuation of the pump spray head 8, the liquid contained in the container 9 can be sprayed.

The second embodiment of FIG. 4 differs from the first embodiment with regard to the type of arrangement of the container 9 in the connecting adapter 3. While in the first embodiment a holder 4 is provided, this embodiment has no such holder. Fixation is realized directly between the connecting adapter 3 and the upper part of the container 9. This can be realized either by friction or by a thread or by a bayonet closure.

The third embodiment of FIG. 5a provides a sleeve 12. The sleeve has a bottom 13 as well as lateral windows 14 in the bottom area. In the upper area, the sleeve 12 has peripheral locking ribs 15. The connecting adapter 3 is also cylindrical. The basic spraying unit 2 is provided therein. It is secured at the top and at the bottom within this connecting adapter 3 in the illustrated way. In the lower peripheral area, the connecting adapter 3 has an annular seal 11 connected thereto by injection molding. Moreover, locking elements matching the locking ribs 15 are provided.

The function is as follows:

First, the container 9 in the form of an ampule is inserted into the sleeve 12 from above after the head of the ampule has been broken off. Subsequently, the connecting adapter 3 of the spraying device 1 is placed from above onto the sleeve 12 and is moved downwardly until the annular seal 11 comes to rest on the shoulder of the container 9 in a seal-tight way. In this position, the locking ribs 15 of the sleeve 12 are locked by the matching locking elements of the connecting adapter 3. With a corresponding configuration of these locking ribs 15, the sleeve 12 and the connecting adapter 3 can be detachably or non-detachably connected.

The illustration of FIG. 5b shows a container 9 having a larger volume so that the container 9 in comparison to the container 9 of the embodiment of FIG. 5a is taller. This container 9 is also inserted into the sleeve 12 and subsequently the connecting adapter 3 is pushed thereon from above. In this case, the connecting adapter 3 does not project so far down as in the embodiment of FIG. 5a because the shoulder of the container 9 is reached earlier.

The container 9 cannot only be in the form of ampules but can also be any type of container 9. Also, the annular seal 11 can engage other areas than the shoulder of the container 9, for example, externally the jacket or internally the area of the removal opening 10.

LIST OF REFERENCE NUMERALS 1 spraying device
2 basic spraying unit
3 connecting adapter
4 holder
5 stay
6 clamping arm
7 ascending pipe
8 spray head
9 container
10 removal opening
11 annular seal
12 sleeve
13 bottom
14 window
15 locking ribs

What is claimed is:

1. A device for spraying a liquid, wherein the liquid is contained in a container that, in an initial state, is a unitary closed container comprising a head to be broken off or sawed off for providing a removal opening, the device comprising:

a pump spraying device that operates by a pumping action and is adapted to be arranged on the removal opening of the container;

the pump spraying device comprising a spraying unit with a spray head and a connecting adapter, wherein the connecting adapter is fixedly connected to the spraying unit and wherein the pumping action of the pump spraying device transports the liquid from the container to the spray head;

wherein the connecting adapter has a remote end remote from the spray head and has an annular seal that is connected to an end face of the remote end and is adapted to rest sealingly against a shoulder of the container about the removal opening;

wherein the connecting adapter is essentially cylindrical;

a sleeve having an upper open end and a lower end, wherein the lower end of the sleeve has a bottom and wherein the sleeve is adapted to receive the container through the upper open end;

wherein an outer diameter of the connecting adapter is matched substantially to an inner diameter of the sleeve;

wherein the sleeve and the connecting adapter are separate parts and wherein the sleeve is detachably connected with the upper open end to the connecting adapter by pushing the sleeve onto the connecting adapter in an axial direction of the connecting adapter such that the connecting adapter is received in the sleeve;

wherein the sleeve is axially slidable relative to the connecting adapter;

wherein the sleeve has inner locking ribs and the connecting adapter has outer locking elements matching the locking ribs, wherein the sleeve is slidable in the axial direction and adjustable relative to the connecting adapter in different relative axial positions for accommodating containers of different length, wherein the different relative axial positions are secured by the locking ribs and the locking elements.

2. The device according to claim 1, wherein the spraying device has an ascending pipe configured to extend into an interior of the container to approximately a bottom of the container.

* * * * *